United States Patent [19]

Wadhwa

[11] 4,440,161

[45] Apr. 3, 1984

[54] MULTIPURPOSE NASAL AIRWAY

[76] Inventor: Rajinder K. Wadhwa, 2482 Mt. Royal Rd., Pittsburgh, Pa. 15217

[21] Appl. No.: 298,501

[22] Filed: Sep. 1, 1981

[51] Int. Cl.³ ............... A61M 25/00; A61M 15/06; A61M 15/08; A61B 17/32

[52] U.S. Cl. ................ 128/202.13; 128/305; 128/305.3; 128/207.18; 30/151

[58] Field of Search ......... 128/207.18, 305.3, 200.26, 128/305, 202.13; 30/151

[56] References Cited

U.S. PATENT DOCUMENTS

| | | | |
|---|---|---|---|
| 973,427 | 10/1910 | Haynes | 128/203.24 |
| 1,390,720 | 9/1921 | Powers | 128/305 |
| 1,444,155 | 2/1963 | Jorgensen | 30/151 |
| 1,611,171 | 12/1926 | Easton | 401/195 |
| 3,021,836 | 2/1962 | Marsden | 128/29 |
| 3,068,590 | 12/1962 | Padellford | 35/17 |
| 3,297,027 | 1/1967 | Rusch | 128/145.5 |
| 3,307,551 | 3/1967 | Violet, Jr. | 128/305.3 |
| 3,395,711 | 8/1968 | Pizak, Jr. | 128/200.26 |
| 3,508,543 | 4/1970 | Aulicino | 128/145.5 |
| 3,706,106 | 12/1972 | Leopoldi | 128/305 |
| 3,861,087 | 1/1975 | Martin | 30/151 |
| 3,964,488 | 6/1976 | Ring et al. | 128/207.18 |
| 3,972,321 | 8/1976 | Proctor | 128/207.18 |
| 4,300,550 | 11/1981 | Gandi et al. | 128/207.18 |

Primary Examiner—Henry J. Recla
Assistant Examiner—Karin M. Reichle
Attorney, Agent, or Firm—Buell, Blenko, Ziesenheim & Beck

[57] ABSTRACT

A nasal airway in a preferred embodiment includes a tubular housing and an airway tube which in the storage position is received at least partially within the tubular housing and in a second position projects outwardly therefrom. The airway tube may have one or more auxiliary openings disposed between the ends thereof. A first closure may close the end of the tubular housing to which the airway tube may be secured and a second closure may close the other end. Tracheotomy blade means may be associated with the second closure. The multipurpose nasal airway may also be provided with writing equipment such as a reservoir of ink and associated discharge point.

13 Claims, 8 Drawing Figures

MULTIPURPOSE NASAL AIRWAY

BACKGROUND OF THE INVENTION

1. Field of the Invention

This invention relates generally to nasal airways and, more specifically, to such airways which are of relatively small size and are adapted to serve as a writing implement as well as providing means for performing an emergency tracheotomy.

2. Description of the Prior Art

It has been known during surgical procedures for anesthesiologists to place an airway into the mouth of a patient. The airway, which generally consists of a curved, plastic tube serves to keep the patient's mouth open and permits ready insertion of tubes for administering anesthesia, withdrawing mucous by suction, as well as other purposes. It is also known to employ airways which are inserted into a patient's mouth in order to initiate emergency resuscitation procedures. U.S. Pat. Nos. 3,021,836 and 3,297,027 show two examples of tubes which are introduced into a patient's mouth for resuscitation purposes. U.S. Pat. No. 3,068,590 discloses a resuscitation training device.

U.S. Pat. No. 3,508,543 discloses a resuscitation tube adapted to be introduced into the patient's mouth and having auxiliary tubes adapted to be introduced into the patient's nostrils.

In respect of most medical emergencies where resuscitation is needed, time is of the essence and, with the exception of hospitals and certain clinics and doctor's offices, in general, airways will not be readily available at the site of the emergency need. As a result of the size, cost and single-purpose nature of known airways, there remains a very real and substantial need for an airway of such design and construction as to be effective in use and to be likely to be available more readily at the scene of an emergency.

SUMMARY OF THE INVENTION

The present invention has met the above-described need by providing a multipurpose airway which is, as a result of its size and multiple uses, more likely to be carried about by physicians and other medically or paramedically trained individuals thereby enhancing the likelihood that the airway will be available where needed when needed.

In the present invention, a nasal airway includes a tubular housing having an associated airway tube which may be stored in a first position and secured for use in a second position. In addition, the article may function as a writing implement and may provide means for performing an emergency tracheotomy. As the nasal airway of the present invention is preferably relatively small, such as the size of a conventional fountain or ballpoint pen, for example, and it is adapted, in one embodiment, to function as a writing implement, this additional function enhances the likelihood that an individual will carry the instrument on his or her person.

It is an object of the present invention to provide a nasal airway which is compact, economical to manufacture and easy to use.

It is a further object of the present invention to provide such a nasal airway which has means permitting it to function as a writing implement.

It is another object of the present invention to provide such a nasal airway which has means for performing an emergency tracheotomy.

It is yet another object of the persent invention to increase the likelihood that emergency resuscitation procedures may be undertaken effectively at the scene of an emergency in prompt fashion.

These and other objects of the invention will be more fully understood from the description of the invention on references to the illustrations appended hereto.

DESCRIPTION OF THE PREFERRED EMBODIMENTS

As used herein, in the absence of an express indication to the contrary at a particular location, the term "patient" shall refer to members of the animal kingdom, including human beings.

Figure 1:
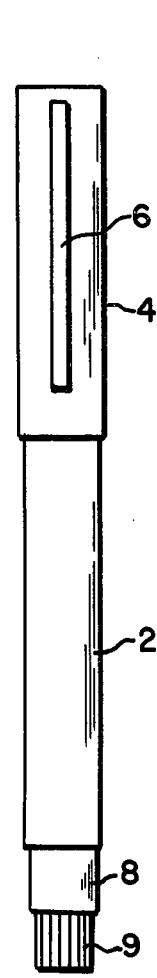
FIG. 1 is a front elevational view of a form of nasal airway assembly of the present invention.

Referring now in greater detail to FIG. 1, there is shown an embodiment of the miniaturized nasal airway of the present invention which may conveniently have the dimensions of a commercially available fountain or ballpoint pen. It may, for example, have a length of about 4 to 6 inches and a width of about ½ to ⅝ inch. In the form shown, the nasal airway has a tubular housing 2 which has a closure 4 provided with a clip 6 so as to secure the same to a pocket and a lower closure 8.

Figure 2:
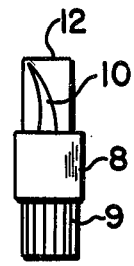
FIG. 2 is a front elevational view of a portion of the airway of FIG. 1 which is adapted to function as a tracheotomy blade.
Figure 3:
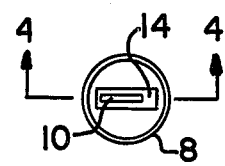
FIG. 3 is a top plan view of the tracheotomy blade of FIG. 2 with the blade protective covering not illustrated.
Figure 4:
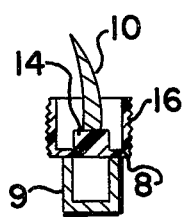
FIG. 4 is a cross sectional illustration of the blade assembly taken through 4—4 of FIG. 3.

Referring now more specifically to FIGS. 2 through 4, the tracheotomy blade feature of the present invention will be considered in greater detail. In the event that the apparatus of the present invention were needed to be employed to perform a tracheotomy on an emergency basis, closure 8, which is preferably threadedly secured to tubular housing 2, would be removed. As removed, it would assume the appearance shown in FIG. 2 wherein the closure 8 and underlying serrated extension 9 may serve as the handle portion for permitting use of the projecting blade member 10. The blade member 10 may advantageously be composed of stainless steel, plastic or other noncorrosive material. In the form shown in FIG. 2, a protective material 12 such as a plastic film is positioned over the blade 10 in order to maintain blade cleanliness, avoid inadvertent cutting by the blade and, in the event of use of a corrosion-susceptible material in the blade, to resist corrosion. The film or cover 12 would be stripped from the blade thereby permitting use of the same.

Referring to FIGS. 3 and 4, it is noted that in order to reinforce the connection between the blade 10 and the closure 8, a pedestal 14 which surrounds and supports the lower portion of the blade is provided.

While in the preferred embodiment of the invention the blade 10 will be presecured to the closure 8, the blade may be provided separately in a compartment in the housing with or without provision for subsequent attachment of the blade to closure 8, if desired.

Figure 5:
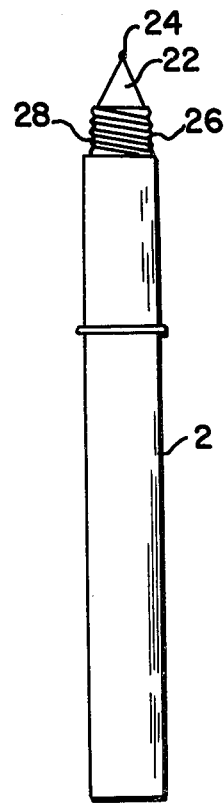
FIG. 5 is a front-elevational view of the nasal airway of FIG. 1 with the closure portions removed.

The external thread 16 on closure 8, shown in FIG. 4, would cooperate with internal threads on the lower portion of housing 2 to permit threaded engagement between closure 8 and tubular housing 2. Referring now in greater detail to FIG. 5, there is shown the nasal airway of the present invention with closures 4 and 8 both removed. As will be noted at the lower end of housing 2, internal threads 20 are provided so as to cooperate with external thread 16 of closure 8.

Referring to the upper portion of FIG. 5, it is noted that in this embodiment a writing implement which has a supply of material to be deposited during writing and means for permitting contact between the material and a writing surface are provided. In the form shown the writing implement is a pen having a cone 22 terminating in a pen point 24 through which ink stored in a reservoir (not shown in this view) may be discharged. The lower portion of the cone 22 has external threads which cooperate with internal threads (not shown) of the end of airway tube 26 so as to permit threaded interengagement therebetween. It is also noted that the airway tube 26 has external threads 28 which cooperate with internal threads (not shown in this view) within the upper portion of housing 2 to permit securement of the airway tube to the housing in a storage position.

Figures 6, 7:
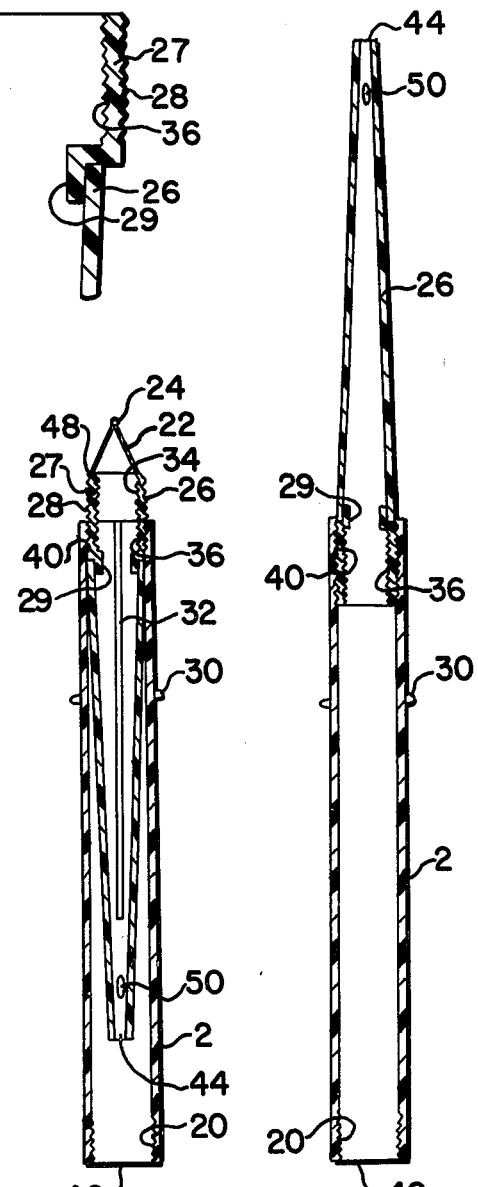
FIG. 6 is a cross-sectional illustration of a form of nasal airway of the present invention showing the airway tube in storage position.
FIG. 7 is a cross-sectional illustration of a form of nasal airway of the present invention showing the airway tube in usable position.

Referring to FIG. 6 in greater detail there is shown a cross sectional illustration of the nasal airway of the present invention. It is noted that the housing 2 is provided with an outwardly projecting annular rib 30 over which closure 4 is adapted to be engaged in snap-fit arrangement. In general, the interior surface of closure 4 generally toward the lower extremity thereof would have an inwardly projecting annular rib which would permit the desired snap-fit securement.

As is shown toward the upper portion of FIG. 6, an ink reservoir 32 is operatively associated with pen cone 22 and external threads 34 on pen cone 22 cooperative with internal threads 36 on the nasal airway tube 26. It is also noted that the external threads 28 on airway tube 26 cooperate with internal threads 40 to secure the airway tube 26 to the housing 2.

In the form shown in FIG. 6, the airway tube 26 is in storage position with a major portion of the tube 26 being disposed within tubular housing 2. In this position the lower end opening 44 of airway tube is disposed closer to the lower end 46 of housing 2 than is the upper end 48 of tube 26. The pen reservoir 32 is received within tube 26. While not shown in this view, the blade 10 may be received within the opening or bore of tube 26, may be positioned beside the same or the relative lengths of tube 26 and blade 10 may be such as to create axial spacing along the housing interior therebetween.

In a preferred form, the airway tube 26 will be composed of a resilient material such as a material selected from the group consisting of natural or synthetic rubber, such as latex, for example or plastic. Also, it is preferred that the outer surface of the airway tube 26 either be composed of a somewhat resilient material or that at least a portion of said tube adjacent tube end 44 be covered by a water soluble lubricant such as lanolin, for example. Also, products sold under the trade designation Acid mantle (buffered aluminum acetate) or the trade designation Aqua-phor may be used. This will serve to facilitate insertion of the tube into the nasal passageway of the patient.

Another feature of the invention illustrated in FIG. 6 is the auxiliary opening 50 in tube 26 which is disposed in relative close proximity to tube end 44. In the event that through mucous or other means blockage of the end 44 occurs, functioning of the airway can continue through opening 50 which has its closest portion preferably spaced about ½ to 1 inch from end 44. It will be appreciated that a plurality of such openings 50 may be provided, if desired.

FIG. 7 shows the airway in the position in which it would appear during usage with the tube 26 projecting outwardly and being threadedly secured to housing 2. The end 44 of nasal airway would be inserted into the patient's nostril and the end 46 of tubular housing 2 would be inserted into the mouth of the individual applying resuscitative procedures.

Figure 8:
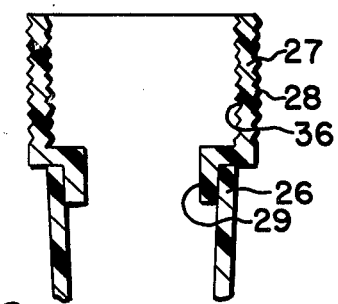
FIG. 8 is a cross sectional illustration of a portion of a nasal airway of the present invention.

FIG. 8 shows a portion of a preferred tube 26 construction. While the tube 26 may be formed as a unitary article, in the form shown in FIG. 8 it is multipiece. The upper sleeve 27 terminates in an inwardly offset downwardly projecting flange 29. The lower portion of the tube 26 is secured, as by self-bonding or adhesive means to the radially outer portion of flange 29. This permits the use of different materials for the two portions of tube 26 without engaging in complex molding procedures.

It will be appreciated that while the principal objective of the present invention is to provide readily available, miniaturized resuscitation equipment and this may be accomplished without providing the tracheotomy blade and the writing instrument such as a pen, in the preferred embodiment of the invention the presence of the tracheotomy blade may be advantageous in respect of numerous emergencies and the pen will not only provide a further function for the apparatus, but also greatly enhance the likelihood that the individual will have the instrument in his or her possession when an emergency occurs.

Assuming that the tracheotomy blade and writing implement are part of the particular embodiment of the invention being carried by an individual, the procedure for operating the same will now be considered. First of all, should a tracheotomy be required, the individual need merely remove closure 8 by unthreading the same from tubular housing 2 and remove the protective covering material 12 from the blade 10 thereby exposing the blade and permitting closure 8 to function as a handle in using the same. Assuming that the airway is to be employed, the pen cone 22 is unthreaded from the airway tube 26 and the airway tube 26 is unthreaded from the tubular housing 2. Subsequently, the airway tube 26 is removed from the housing 2, is reversed and then threadedly connected to the housing at either thread 20 or thread 36 thereby permitting insertion of the airway tube 26 into the patient's trachea (or in the event of no tracheotomy, into the nostril) and administration of air or other material through end 46 of housing 2. The sequence in which these two unthreading operations is accomplished is not critical. If desired, the tube 26 could be removed from housing 2 first and subsequently the pen cone 22 removed from tube 26.

It will be appreciated, therefore, that the present invention provides an economical and effective means for starting emergency medical treatment when resuscitation is needed by way of airway or a tracheotomy need be performed. All of this is accomplished while permitting the apparatus to function as a writing implement thereby providing another dimension of utility and enhancing the likelihood that the instrument will be present during an emergency need.

Whereas particular embodiments of the invention have been described above for purposes of illustration, it will be evident to those skilled in the art that numerous variations of the details may be made without departing from the invention as defined in the appended claims.

I claim:

1. A nasal airway comprising a tubular housing having a first threaded portion adjacent a first end thereof,
   an airway tube having a threaded end and a free end insertable into a patient's nostril,
   said airway tube received within said tubular housing in a storage position,
   said airway tube, when in said storage position, having said free end within said tubular housing and said threaded end being threadedly secured to said first threaded portion of said tubular housing,
   first closure means removably covering said first end,
   said tubular housing having a second end,
   second closure means removably covering said second end,
   tracheotomy blade means operably connected to said second closure so as to be disposed within said second end of said housing whereby removal of said second closure from the second end of said housing will permit separation of said tracheotomy blade, means from said housing for use,
   writing means having a supply of material to be deposited during writing extending into said airway tube and being removably secured to the threaded end of said airway tube and having a material discharge end underlying said first closure means, whereby removal of said first closure means, said second closure means and said writing means from said tubular housing will permit separation of said airway tube from said housing and threaded attachment of said airway tube threaded end to said housing first threaded end with said airway tube free end disposed exteriorly of said housing to create a nasal airway consisting of said housing and said airway tube.

2. The nasal airway of claim 1 including said writing means including pen means having an ink reservoir operatively associated with a discharge point.

3. The nasal airway of claim 2 including said pen means reservoir extending into said airway tube when said airway tube is in said first storage position.

4. The nasal airway of claim 3 including said pen means having a threaded end adjacent said discharge point to threadedly secure said pen means to said airway tube.

5. The nasal airway of claim 1 including said airway tube having at least one auxiliary opening spaced from the ends of said airway tube.

6. The nasal airway of claim 5 including said auxiliary opening being disposed closer to said free end of said airway tube than to the threaded end of said airway tube.

7. The nasal airway of claim 6 including said auxiliary opening being disposed about ½ to 1 inch from said free end of said airway tube.

8. The nasal airway of claim 1 including said airway tube being composed of a resilient material.

9. The nasal airway of claim 8 including said airway tube being composed of a material selected from the group consisting of rubber and plastic.

10. The nasal airway of claim 9 including lubricant means disposed on at least a portion of the exterior of said airway tube.

11. The nasal airway of claim 1 including said tracheotomy blade means secured to said second closure, whereby said second closure may function as a handle for said blade means.

12. The nasal airway of claim 11 including said second closure having a threaded portion whereby said second closure is threadedly secured to said tubular housing with said blade means disposed within said housing.

13. The nasal airway of claim 12 including removable protective means secured to said tracheotomy blade.

* * * * *

UNITED STATES PATENT AND TRADEMARK OFFICE
CERTIFICATE OF CORRECTION

PATENT NO. : 4,440,161
DATED : April 3, 1984
INVENTOR(S) : Rajindar K. Wadhwa

It is certified that error appears in the above-identified patent and that said Letters Patent is hereby corrected as shown below:

On the title page, [76] Inventor:
  change the inventor's name from "Rajinder" to --Rajindar--

In the References, Patent 973,427, change "Haynes" to --Hayes--

In the References, Patent 1,444,155, change "2/1963" to --2/1923--

Column 3, line 46, change "cooperative" to --cooperate--

Signed and Sealed this

Thirteenth Day of November 1984

[SEAL]

Attest:

Attesting Officer

GERALD J. MOSSINGHOFF
Commissioner of Patents and Trademarks